United States Patent [19]
Hörold

[11] Patent Number: 5,773,533
[45] Date of Patent: Jun. 30, 1998

[54] EPOXY RESIN REACTED WITH CARBOXY-FUNCTIONAL PHOSPHINIC OR PHOSPHONIC ACID AND HARDENER

[75] Inventor: Sebastian Hörold, Erftstadt, Germany

[73] Assignee: Hoechst Aktiengesellschaft, Frankfurt, Germany

[21] Appl. No.: 827,434

[22] Filed: Mar. 27, 1997

[30] Foreign Application Priority Data

Apr. 1, 1996 [DE] Germany ............ 196 13 067.0

[51] Int. Cl.⁶ ............ C08G 59/14; C08L 63/00; C08L 63/02
[52] U.S. Cl. ............ 525/533; 523/427; 523/428; 523/457; 523/466; 525/423; 525/481; 525/485; 525/524; 525/526; 525/508; 528/108
[58] Field of Search ............ 528/108; 525/508, 525/423, 481, 485, 524, 526, 533; 523/427, 428, 457, 466

[56] References Cited

U.S. PATENT DOCUMENTS

| | | | |
|---|---|---|---|
| 3,334,110 | 8/1967 | Schramm | 260/307 |
| 3,477,982 | 11/1969 | Delft et al. | 260/37 |
| 4,272,647 | 6/1981 | Veit et al. | 179/1 AL |
| 4,280,951 | 7/1981 | Saito et al. | 528/108 |
| 5,294,265 | 3/1994 | Gray et al. | 148/250 |
| 5,364,893 | 11/1994 | von Gentzkow et al. | 523/429 |
| 5,648,171 | 7/1997 | von Gentzkow et al. | 525/108 |

FOREIGN PATENT DOCUMENTS

| | | |
|---|---|---|
| 2158361 | 9/1994 | Canada . |
| 0384939 | 9/1990 | European Pat. Off. . |
| 1745796 | 3/1972 | Germany . |
| 2518144 | 11/1976 | Germany . |
| 2540283 | 3/1977 | Germany . |
| 3540524 | 5/1987 | Germany . |
| 4308185 | 9/1994 | Germany . |
| 6-80765 | 3/1994 | Japan ............ 525/108 |
| 1517865 | 7/1978 | United Kingdom . |

OTHER PUBLICATIONS

*Lackkunstharze* (Wagner/Sarx), 5th ed., Carl Hanser Verlag (1971), pp. 174–194.

Bald, g., et al, *Angewandte Makromol. Chem.* 44:151–163 (1975).

*Primary Examiner*—Robert E. Sellers
*Attorney, Agent, or Firm*—Connolly and Hutz

[57] ABSTRACT

The invention relates to flame-resistant epoxy resin mixtures comprising epoxy resins, phosphorus-containing compounds and a hardener, which comprise a phosphorus-containing compound of the formula I or II

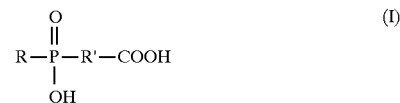

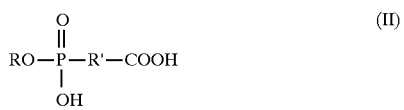

in which R is a linear or branched alkyl, cycloalkyl, aryl or alkylaryl group having 1 to 18 carbon atoms or is hydrogen, and R' is a linear or branched alkylene, cycloalkylene, arylene or alkylarylene group having 1 to 18 carbon atoms, to a process for their preparation and to their use.

9 Claims, No Drawings

EPOXY RESIN REACTED WITH CARBOXY-FUNCTIONAL PHOSPHINIC OR PHOSPHONIC ACID AND HARDENER

The present invention relates to phosphorus-modified epoxy resin mixtures comprising epoxy resins, phosphorus-containing compounds and a hardener (curing agent), to a process for their preparation and to their use.

Epoxy resins are nowadays employed for the production of molding compositions and coatings having good thermal, mechanical and electronic properties. They are suitable for encapsulating electrical and electronic components and for soak and impregnation processes. In electrical engineering, the epoxy resin molding compositions used are predominantly given a flame-resistant treatment.

Epoxy resin molding compositions are in general given a flame-resistant treatment using bromine-containing aromatic compounds, especially tetrabromobisphenol A. If exclusively brominated flameproofing agents are employed, then a bromine content of about 20% is necessary in order to ensure that the molding compositions are self-extinguishing. As a synergist, antimony trioxide is frequently used. In the event of a fire, hydrogen bromide is given off, which may lead to corrosion damage. Under adverse conditions it is also possible for polybrominated dibenzodioxins and furans to be formed. There is therefore a need for epoxy resin molding compositions which achieve the required flame resistance without the addition of brominated compounds.

For the flame-resistant treatment of epoxy resin molding compositions, fillers having an extinguishing action, such as aluminum oxide hydrate (DE 35 40 524 A1), have been proposed. Through the addition of ammonium polyphosphate, alone or in combination with aluminum oxide hydrate, it is also possible to achieve adequate flame resistance. Instead of ammonium polyphosphate, red phosphorus can also be used (DE 17 45 796 A1).

A disadvantage of all the flameproofing agents present as fillers is that the materials obtained are not transparent. Numerous liquid organophosphorus compounds have already been proposed as flame-retarding plastics additives. A disadvantage with these systems, however, is the pronounced "plasticizer effect" of these additives. In the case of cured epoxy resins, the plasticizing effect manifests itself in a marked reduction in the glass transition temperature.

The flame-resistant treatment of epoxy resins with epoxide-functional phosphonic esters has already been described (EP 0 384 939 A1). A disadvantage with these systems is the great complexity of synthesis of such phosphonic esters. Also known in the literature are phosphorus-modified epoxy resins which are obtainable by reacting polyepoxide compounds with anhydrides of phosphonic acids or phosphinic acids and which are notable for their flame-resistant properties (DE 43 08 185 A1). Easier to obtain industrially than the anhydrides are carboxy-functional phosphonic and phosphinic acids. Products of this kind are already being used for the flame-resistant treatment of polyester fibers.

The object of the invention was to provide phosphorus-modified epoxy resin mixtures which are of high flame resistance, are easy to prepare and are versatile.

This object is achieved by flame-resistant epoxy resin mixtures of the type described at the outset, which comprise a phosphorus-containing compound of the formula I or II

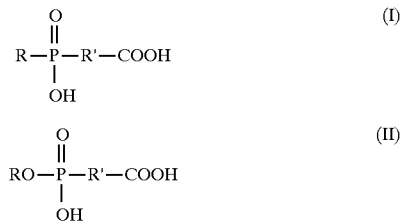

in which R is linear or branched alkyl, cycloalkyl, aryl or alkylaryl groups having 1 to 18, preferably 1 to 16 carbon atoms, or is hydrogen, and R' is linear or branched alkylene, cycloalkylene, arylene or alkylarylene groups having 1 to 18, preferably 1 to 6 carbon atoms and, with particular preference, 1–2 carbon atoms.

The flame-resistant epoxy resin mixture preferably contains from 10 to 100 parts by weight of phosphorus-containing compounds of the formula I or II per 100 parts by weight of epoxy resin, the overall weight ratio of epoxy resin and phosphorus-containing compound of formula I or II to hardener being 1:1 to 10:1.

The flame-resistant epoxy resin mixture is preferably free from halogen.

The flame-resistant epoxy resin mixture preferably contains from 5 to 300 parts by weight per 100 parts weight of epoxy resin of phosphorus-free epoxy resins.

The flame-resistant epoxy resin mixture preferably contains from 5 to 300 parts by weight per 100 parts weight of epoxy resin of further ingredients and/or fillers.

The flame-resistant epoxy resin mixture preferably contains from 0.5 to 13% by weight of phosphorus based on the combined weight of epoxy resin and phosphorus-containing compound.

The flame-resistant epoxy resin mixture particularly preferably contains from 1 to 6% by weight of phosphorus based on the combined weight of epoxy resin and phosphorus-containing compound.

The flame-resistant epoxy resin mixture preferably contains an accelerator.

The present object is likewise achieved by a process for preparing flame-resistant epoxy resin mixtures comprising epoxy resins, phosphorus-containing compounds and a hardener, which in a first reaction step comprises reacting an epoxy resin with a phosphorus-containing compound of the formula I or II and then, in a second reaction step, comprises converting the reaction product into the flame-resistant epoxy resin mixture, with a hardener.

The first reaction step preferably takes place in a solvent.

Preferred aprotic polar solvents employed are N-methylpyrrolidone, dimethylformamide, tetrahydrofuran, dioxane, dialkyl ethers, glycol ethers, ketones and/or esters.

Also suitable are ethylene glycol ethers, propylene glycol ethers, butylene glycol ethers of monoalcohols having optionally branched alkyl radicals of 1 to 6 carbon atoms, and also ketones, such as acetone, methyl ethyl ketone, methyl isopropyl ketone, methyl isobutyl ketone, cyclohexanone and the like; esters, such as ethyl acetate, butyl acetate, ethylene glycol acetate and methoxypropyl acetate, can also be employed.

Other preferred solvents are halogenated hydrocarbons, aliphatic, cycloaliphatic and/or aromatic hydrocarbons, employed individually or as mixtures. Of these, preference is given to hexane, heptane, cyclohexane, toluene and dixylenes.

The reaction in the first reaction step preferably takes place at temperatures of between -10° and +200° C.

With particular preference, the reaction takes place at temperatures from 70° to 130° C.

The reaction in the second reaction step preferably takes place at temperatures from 0° to 200° C.

With particular preference, this reaction takes place at temperatures from 100° to 180° C.

The carboxy-functional phosphinic acids and phosphonic acids on which the invention is based can be prepared, for example, by addition reaction of suitable phosphorus compounds with acrylic acid or acrylic esters.

The phosphorus compound can preferably be methanephosphonous dichloride. Addition reaction with acrylic acid, and subsequent hydrolysis, gives carboxyethylmethylphosphinic acid (DE 25 40 283 A1) (III). Similarly, it is also possible to use phenylphosphonous dichloride.

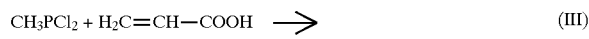

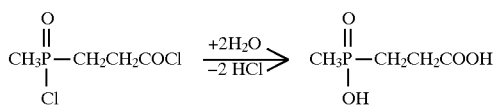

The carboxy-functional phosphonic acids can be prepared, for example, by addition reaction of dialkyl or diaryl phosphites with acrylic esters and subsequent partial or complete hydrolysis (e.g. DE 25 18 144 A1) (IV).

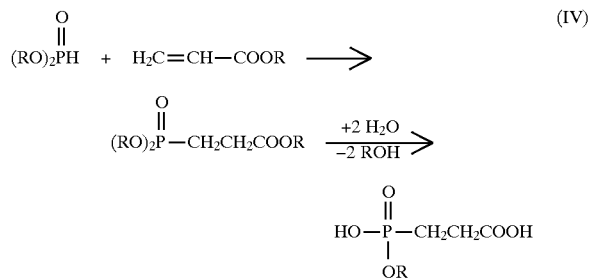

The carboxy-functional phosphonic acids are also obtainable from phosphonous triesters and halogen-substituted acetals, in the manner of the Arbuzov reaction, and subsequent hydrolysis (V).

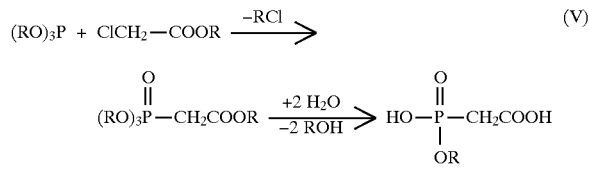

The halogen-free epoxide compounds employed in accordance with the invention (also referred to below as polyepoxide compounds) can be saturated or unsaturated and aliphatic, cycloaliphatic, aromatic and/or heterocyclic. They may additionally comprise those substituents which under the conditions of mixing or reaction do not give rise to any disruptive side reactions, examples being alkyl or aryl substituents, ether groups or the like. It is also possible to use mixtures of different polyepoxide compounds. The mean molecular weight $M_n$ of these polyepoxide compounds can be up to about 9000 but is generally from about 150 to 4000.

Examples of these polyepoxide compounds are polyglycidyl ethers based on polyhydric, preferably dihydric alcohols, phenols, hydrogenation products of these phenols and/or on novolaks (reaction products of mono- or polyhydric phenols, such as phenol and/or cresols, with aldehydes, especially formaldehyde, in the presence of acidic catalysts), that are obtained in a known manner, for example by reacting the respective polyols with epichlorohydrin.

Examples of polyhydric phenols that may be mentioned here are: resorcinol, hydroquinone, 2,2-bis(4-hydroxyphenyl)-propane (bisphenol A), isomer mixtures of dihydroxy-diphenylmethane (bisphenol F), 4,4'-dihydroxydiphenyl-cyclohexane, 4,4,'-dihydroxy-3,3'-dimethyldiphenylpropane, 4,4'-dihydroxybiphenyl, 4,4'-dihydroxybenzophenone, 1,1-bis(4-hydroxyphenyl)ethane, 1,1'-bis(4-hydroxyphenyl)isobutane, 2,2-bis(4-hydroxy-tert-butylphenyl)propane, bis(2-hydroxynaphthyl)methane, 1,5-dihydroxynaphthalene, tris(4-hydroxyphenyl)methane, 1,1'-bis(4-hydroxyphenyl) ether. Among these, bisphenol A and bisphenol F are preferred.

Also suitable as polyepoxide compound are the polyglycidyl ethers of polyhydric aliphatic alcohols. Examples of such polyhydric alcohols that may be mentioned are 1,4-butanediol, 1,6-hexanediol, polyalkylene glycols, glycerol, trimethylolpropane, 2,2-bis(4-hydroxy-cyclohexyl)propane and pentaerythritol.

Further suitable polyepoxide compounds are (poly) glycidyl esters which are obtained by reacting epichlorohydrin or similar epoxy compounds with an aliphatic, cycloaliphatic or aromatic polycarboxylic acid, such as oxalic acid, adipic acid, glutaric acid, phthalic, isophthalic, terephthalic, tetrahydrophthalic or hexahydrophthalic acid, 2,6-naphthalenedicarboxylic acid and dimerized fatty acids. Examples thereof are diglycidyl terephthalate and diglycidyl hexahydrophthalate. Moreover, polyepoxide compounds which contain the epoxide groups in random distribution over the molecule chain and which can be prepared by emulsion copolymerization using olefinically unsaturated compounds th at contain these epoxide groups, such as, for example, glycidyl esters of acrylic or methacrylic acid, can be employed with advantage in some cases.

Examples of further polyepoxide compounds that can be used are those based on heterocyclic ring systems, for example hydantoin epoxy resins, triglycidyl isocyanurate and/or its oligomers, triglycidyl-p-aminophenol, triglycidyl-p-aminodiphenyl ether, tetraglycidyldiaminodiphenylmethane, tetraglycidyldiaminodiphenyl ether, tetrakis (4-glycidyloxyphenyl) ethane, urazole epoxides, uracil epoxides, oxazolidinone-modified epoxy resins. Other examples are polyepoxides based on aromatic amines, such as aniline, for example N,N-diglycidylaniline, diaminodiphenylmethane and N,N-dimethylaminodiphenylmethane or N,N-dimethylaminodiphenyl sulfone. Further suitable polyepoxide compounds are described in the "Handbook of Epoxy Resins" by Henry Lee and Kris Neville, McGraw-Hill Book Company, 1967, in th e monograph by Henry Lee "Epoxy Resins", American Chemical Society, 1970, in Wagner/Sarx, "Lackkunstharze" Carl Hanser Verlag (1971), 5th edition, 174 ff., in "Angew. Makromol. Chemie", Vol. 44 (1975), pages 151 to 163, in DE 27 57 733 A1 and in EP 0 384 939 A1, which are incorporated herein by reference.

Polyepoxide compounds preferably employed are bisglycidyl ethers based on bisphenol A, bisphenol F and bisphenol S (reaction products of these bisphenols and epichloro-(halo)hydrin) or oligomers thereof, polyglycidyl ethers of phenol-formaldehyde and/or cresol-formaldehyde novolaks, and also diglycidyl esters of phthalic, isophthalic, terephthalic, tetrahydrophthalic and/or hexahydrophthalic acid and of trimellitic acid, N-glycidyl compounds of aromatic amines and heterocyclic nitrogen bases, such as N,N-diglycidylaniline, N,N,O-triglycidyl-p-aminophenol, triglycidyl isocyanurate and N,N,N',N'-tetraglycidylbis(p-aminophenyl)methane, hydantoin epoxy resins and aracid epoxy resins, and also di- and polyglycidyl compounds of polyhydric aliphatic alcohols such as 1,4-butanediol, trimethylolpropane and polyalkylene glycols.

Furthermore, oxazolidinone-modified epoxy resins are also suitable. Compounds of this kind are already known (see: "Angew. Makromol. Chem.", Vol 44, (1975), pages 151 to 163, and US-A 3 334 110); an example thereof that may be mentioned is the reaction product of bisphenol A diglycidyl ether with diphenylmethane diisocyanate (in the presence of an appropriate accelerator). In connection with the preparation of the novel coating composition, the polyepoxy resins can be present individually or in a mixture.

The term "curing" as used herein denotes the conversion of the soluble, meltable polyepoxides to solid, insoluble and infusible, three-dimensionally crosslinked products, generally with simultaneous shaping, in order to give, for instance, impregnated structures, coatings and adhesive bonds.

Examples of hardeners (curing agents) that can be employed are aliphatic, cycloaliphatic, aromatic and heterocyclic amines, such as bis(4-aminophenyl)methane, aniline-formaldehyde resins, bis(4-aminophenyl) sulfone, ethylenediamine, 1,3-propanediamine, hexamethylenediamine, diethylenetriamine, triethylenetetramine, 2,2,4-trimethyl-1,6-hexanediamine, m-xylylenediamine, bis-(4-aminocyclohexyl)methane, 2,2-bis(4-aminocyclohexyl)propane, 3-aminomethyl-3,5,5-trimethylcyclohexylamine (isophoronediamine), polyamidoamines, polyphenols, such as hydroquinone, resorcinol, 2,2-bis(4-hydroxyphenyl) propane (bisphenol A) and phenol-aldehyde resins, polycarboxylic acids and their anhydrides, for example phthalic anhydride, tetrahydrophthalic anhydride, hexahydrophthalic anhydride and pyromellitic dianhydride. In addition to these it is also possible to use catalytic curing agents, such as cyanoguanidines, or Friedel-Crafts catalysts, such as boron trifluoride.

Where amines are used as curing agents, they are normally employed in an amount of from 0.75 to 1.25 equivalents per epoxide equivalent. In the case of polycarboxylic acids or their anhydrides, from 0.4 to 1.1 equivalents are used per epoxide equivalent.

Suitable accelerators are principally imidazole derivatives, for example 2-methylimidazole, 2-phenylimidazole and 2-heptadecylimidazole; also suitable are phosphines, metal soaps and acetylacetonates.

Examples of suitable reactive diluents are mono- or polyfunctional alcohols of low molecular mass, which are reacted with epichlorohydrin.

By varying the ratio of equivalents of polyepoxide compound to carboxy-functional phosphinic acid/phosphonic acid it is possible to adjust the phosphorus content of the novel resin. The ratio of equivalents is preferably between 1:0.1 and 1:0.8, and particularly preferably between 1:0.1 and 1:0.4.

Where solvents are employed they are aprotic and preferably polar. Examples thereof are:

N-methylpyrrolidone, dimethylformamide, ethers, such as diethyl ether, tetrahydrofuran, dioxane, ethylglycol ethers, propylene glycol ethers, butylglycol ethers of monoalcohols having an optionally branched alkyl radical of 1 to 6 carbon atoms.

Examples of other solvents are ketones, such as acetone, methyl ethyl ketone, methyl isopropyl ketone, methyl isobutyl ketone, cyclohexanone and the like, although it is also possible to employ esters, such as ethyl acetate, butyl acetate, ethylene glycol acetate and methoxypropyl acetate. Other suitable solvents are halogenated hydrocarbons and also cycloaliphatic and/or aromatic hydrocarbons, preference being given to hexane, heptane, cyclohexane, toluene and dixylenes. It is possible to employ these solvents individually or in a mixture.

The epoxy resin molding compositions are preferably reinforced by means of glass cloth or glass fibers. The epoxy resin molding compositions can also be equipped with fillers, such as quartz flour or aluminum oxide hydrate.

Testing of the fire behavior was carried out in accordance with the directions from Underwriters Laboratories "Test for Flammability of Plastic Materials—UL 94" in the version of 05.02.1975 on test specimens 127 mm in length, 12.7 mm in width and of various thicknesses. The oxygen index was determined in an apparatus in accordance with ASTM-D 2863-74.

The novel epoxy resin molding compositions can be used for surface coating. They can be used for encapsulating electrical components, for laminates and for adhesives.

The invention is illustrated below by examples:

I. PREPARATION OF THE PHOSPHORUS-MODIFIED EPOXY RESINS

EXAMPLE 1

(with 2-carboxyethanemethanephosphinic acid)

200 g of a bisphenol A bisglycidyl ether having an epoxide value of 5.5 mol/kg are charged to a 500 ml five-necked flask with reflux condenser, stirrer shaft, thermometer and solids metering port. At a bath temperature of 100° C., 41 g (0.27 mol) of 2-carboxyethanemethanephosphinic acid are added in portions. After 30 minutes, a clear solution having an epoxide value of 3.1 mol/kg is obtained. After stirring for 4 h more at 100° C., an epoxy resin which is solid at room temperature and has an epoxide value of 2.4 mol/kg and a phosphorus content of 3.5% by weight is obtained.

EXAMPLE 2

(with 2-carboxyethanemethanephosphinic acid)

100 g of a bisphenol A bisglycidyl ether having an epoxide value of 5.5 mol/kg are charged to a 500 ml five-necked flask with reflux condenser, stirrer shaft, thermometer and solids metering port. At a bath temperature of 100° C., 30.8 g (0.2 mol) of 2-carboxyethanemethanephosphinic acid are added in portions. After stirring for 2.5 h more at 100° C., an epoxy resin which is solid at room temperature and has an epoxide value of 1.3 mol/kg and a phosphorus content of 4.7% by weight is obtained.

EXAMPLE 3

(with 2-carboxyethanemethanephosphinic acid)

842 g of a bisphenol A bisglycidyl ether having an epoxide value of 5.5 mol/kg and 234.8 g of 2-carboxyethanemethanephosphinic acid are charged to a 2 l five-necked flask with reflux condenser, stirrer shaft, thermometer and solids metering port. The mixture is stirred at 95° C. for 1 h. Then 335 ml of methyl ethyl ketone are metered in at 95° C. over the course of 2 h. After stirring for a further 2 h, an 80% strength solution of a phosphorus-modified epoxy resin is obtained. The epoxide value is 1.7 mol/kg, the phosphorus content 3.4% by weight. After storage at room temperature for 12 days, the epoxide value is 1.7 mol/kg.

EXAMPLE 4

(with monomethyl 2-carboxyethanephosphonate)

264 g of a bisphenol A bisglycidyl ether having an epoxide value of 5.5 mol/kg are charged to a 500 ml five-necked flask with reflux condenser, stirrer shaft, thermometer and solids metering port. At a bath temperature of 120° C. under a gentle vacuum (250 mm), 67 g (0.36 mol) of mono-methyl 2-carboxyethanephosphonate, dissolved in 50 ml of methyl ethyl ketone, are added over the course of 30 minutes. The solvent is removed by distillation. After stirring for a further 30 minutes at 120° C., 328.7 g of an epoxy resin which is solid at room temperature and has an epoxide value of 1.3 mol/kg and a phosphorus content of 3.4% by weight are obtained.

EXAMPLE 5
(with monoethyl carboxymethanephosphonate)

79 g of a bisphenol A bisglycidyl ether having an epoxide value of 5.5 mol/kg and 20 ml of methyl ethyl ketone are charged to a 250 ml five-necked flask with reflux condenser, stirrer shaft, thermometer and solids metering port. At a bath temperature of 75° C., 18.25 g of monoethyl carboxymethanephosphonate (0.1 mol) dissolved in 15 ml of methyl ethyl ketone are added over the course of 30 minutes. The solvent is removed by distillation. After stirring for a further 2 h at 75° C., 100.7 g of an epoxy resin which is solid at room temperature and has an epoxide value of 1.8 mol/kg and a phosphorus content of 3.1% by weight are obtained.

EXAMPLE 6
(with 2-carboxyethanephenylphosphinic acid)

103 g of a bisphenol A bisglycidyl ether having an epoxide value of 5.5 mol/kg are charged to a 250 ml five-necked flask with reflux condenser, stirrer shaft, thermometer and solids metering port. At a bath temperature of 120° C., 28 g (0.14 mol) of 2-carboxyethanephenylphosphinic acid are added in portions. After 30 minutes, a clear solution having an epoxide value of 2.7 mol/kg is obtained. After stirring for a further 30 minutes at 120° C., an epoxy resin which is solid at room temperature and has an epoxide value of 2.5 mol/kg and a phosphorus content of 3.3% by weight is obtained.

EXAMPLE 7
(with 2-carboxyethanephenylphosphinic acid)

100 g of a bisphenol A bisglycidyl ether having an epoxide value of 5.5 mol/kg are charged to a 250 ml five-necked flask with reflux condenser, stirrer shaft, thermometer and solids metering port. At a bath temperature of 120° C., 41.1 g (0.2 mol) of 2-carboxyethanephenylphosphinic acid are added in portions. After 30 minutes, a clear solution is obtained. After stirring for a further 30 minutes at 120° C., an epoxy resin which is solid at room temperature and has an epoxide value of 1.5 mol/kg and a phosphorus content of 4.5% by weight is obtained.

II. PREPARATION OF THE EPOXY RESIN MOLDING COMPOSITIONS

EXAMPLE 8

100 g of phosphorus-modified epoxy resin from Example 1 are melted at 120° C. and mixed thoroughly with 3.1 g of micronized dicyandiamide (®Dyhard 100 SF, SKW Trostberg AG) and 0.3 g of imidazole accelerator (®Dyhard MI, SKW Trostberg AG), and the mixture is cured in a Teflon mold measuring 200×200×2 mm in a drying oven at 150–180° C. for 4 h. Test specimens measuring 127 mm in length and 12.7 mm in width were sawn from this molded composition.

EXAMPLE 9

100 g of phosphorus-modified epoxy resin from Example 2 are melted at 120° C. and mixed thoroughly with 22 g of methylcyclohexane dicarboxylic anhydride and 0.4 g of benzyldimethylamine, and the mixture is cured in a Teflon mold measuring 200 x 200 x 2 mm in a drying oven at 120–180° C. for 4 h. Test specimens measuring 127 mm in length and 12.7 nm in width were sawn from this molded composition.

EXAMPLE 10

120 g of phosphorus-modified epoxy resin from Example 6 are melted at 120° C. and mixed thoroughly with 3.3 g of micronized dicyandiamide (®Dyhard 100 SF, SKW Trostberg AG) and 0.3 g of imidazole accelerator (®Dyhard MI, SKW Trostberg AG), and the mixture is cured in a Teflon mold measuring 200×200×2 mm in a drying oven at 150–180° C. for 4 h. Test specimens measuring 127 mm in length and 12.7 mm in width were sawn from this molded composition.

EXAMPLE 11

100 g of phosphorus-modified epoxy resin from Example 7 are melted at 120° C. and mixed thoroughly with 25 g of methylcyclohexanedicarboxylic anhydride and 0.4 g of benzyldimethylamine, and the mixture is cured in a Teflon mold measuring 200×200×2 mm in a drying oven at 120–180° C. for 4 h. Test specimens measuring 127 mm in length and 12.7 mm in width were sawn from this molded composition.

EXAMPLE 12 (comparison example)

150 g of a bisphenol A bisglycidyl ether (®Beckopox EP 140) having an epoxide value of 0.53 mol/100 g are melted at 120° C. and mixed thoroughly with 6.9 g of micronized dicyandiamide (®Dyhard 100 SF, SKW Trostberg AG) and 0.3 g of imidazole accelerator (Dyhard MI, methylimidazole, SKW Trostberg AG), and the mixture is cured in a Teflon mold measuring 200×200×2 mm in a drying oven at 150–180° C. for 4 h. Test specimens measuring 127 mm in length and 12.7 mm in width were sawn from this molded composition.

Testing of the fire behavior was carried out in accordance with the directions from Underwriters Laboratories "Test for Flammability of Plastic Materials—UL 94" in the version of 05.02.1975 on test specimens 127 mm in length, 12.7 mm in width and 2 mm in thickness. The oxygen index was determined in an apparatus in accordance with ASTM-D 2863-74.

Table 1 shows the results of the oxygen index measurements and of the fire test in accordance with UL 94.

| Epoxy resin molding composition | Oxyen index | After-burning time | UL 94 classification |
|---|---|---|---|
| Example 8 | 38.1 | <1', <1' | V-0 |
| Example 9 | 26.1 | <1', <1' | V-0 |
| Example 10 | 29.2 | <2',.<2' | V-0 |
| Example 11 | 25.3 | <1', <1' | V-0 |
| Example 12 (comparison example) | 20.5 | burnt up | n.c.* |

*n.c. = not classifiable

I claim:
1. A flame-resistant epoxy resin mixture comprising an epoxy resin reacted with a phosphorus-containing compound and a hardener, the phosphorus-containing compound having the formula I or II

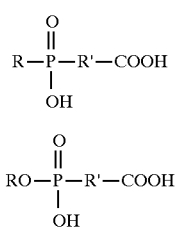

in which R is a linear or branched alkyl, cycloalkyl, aryl or alkylaryl group having 1 to 18 carbon atoms, or is hydrogen, and R' is a linear or branched alkylene, cycloalkylene, arylene or alkylarylene group having 1 to 18 carbon atoms.

2. A flame-resistant epoxy resin mixture as claimed in claim 1, which contains from 10 to 100 parts by weight of the phosphorus-containing compound of the formula I or II per 100 parts by weight of epoxy resin, and wherein the overall weight ratio of epoxy resin and phosphorus-containing compound of formula I or II to hardener is from 1:1 to 10:1.

3. A flame-resistant epoxy resin mixture as claimed in claim 1, which is free from halogen.

4. A flame-resistant epoxy resin mixture as claimed in claim 1, which contains from 5 to 300 parts by weight per 100 parts by weight of epoxy resin of a phosphorus-free epoxy resin.

5. A flame-resistant epoxy resin mixture as claimed in claim 1, which contains from 5 to 300 parts by weight per 100 parts by weight of epoxy resin of glass cloth, glass fibers or a filler other than glass cloth or glass fibers.

6. A flame-resistant epoxy resin mixture as claimed in claim 1, which contains from 0.5 to 13% by weight of phosphorus based on the combined weight of epoxy resin and phosphorus-containing compound.

7. A flame-resistant epoxy resin mixture as claimed in claim 1, which contains from 1 to 6% by weight of phosphorus based on the combined weight of epoxy resin and phosphorus-containing compound.

8. A flame-resistant epoxy resin mixture as claimed in claim 1, which contains an accelerator.

9. A coating composition comprising the epoxy resin mixture as claimed in claim 1.

* * * * *